US012514965B2

(12) United States Patent
Stoehlein et al.

(10) Patent No.: US 12,514,965 B2
(45) Date of Patent: Jan. 6, 2026

(54) METHOD FOR CHECKING THE FUNCTIONALITY OF CONVEYING DEVICES OF A MEDICAL TREATMENT APPARATUS, AND APPARATUSES

(71) Applicant: Fresenius Medical Care Deutschland GmbH, Bad Homburg (DE)

(72) Inventors: Dieter Stoehlein, Herlheim (DE); Juergen Schueller, Bad Koenigshofen (DE); Walter Ehrenberger, Gerolzhofen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 392 days.

(21) Appl. No.: 18/006,505

(22) PCT Filed: Jul. 22, 2021

(86) PCT No.: PCT/EP2021/070529
§ 371 (c)(1),
(2) Date: Jan. 23, 2023

(87) PCT Pub. No.: WO2022/018203
PCT Pub. Date: Jan. 27, 2022

(65) Prior Publication Data
US 2023/0293786 A1 Sep. 21, 2023

(30) Foreign Application Priority Data
Jul. 24, 2020 (DE) ......................... 102020119654.7

(51) Int. Cl.
*A61M 1/16* (2006.01)

(52) U.S. Cl.
CPC ....... *A61M 1/1601* (2014.02); *A61M 2205/15* (2013.01); *A61M 2205/3331* (2013.01); *A61M 2205/3368* (2013.01)

(58) Field of Classification Search
CPC ............ A61M 1/1601; A61M 2205/15; A61M 2205/3331; A61M 2205/3368;
(Continued)

(56) References Cited

U.S. PATENT DOCUMENTS 5,263,367 A 11/1993 Pippert
5,629,871 A 5/1997 Love et al.
(Continued)

FOREIGN PATENT DOCUMENTS

DE 102011106113 1/2013
DE 102017206877 10/2018
(Continued)

OTHER PUBLICATIONS

International Search Report and Written Opinion in International Appln. No. PCT/EP2021/070529, mailed Oct. 25, 2021, 20 pages (with English translation).

*Primary Examiner* — Leslie R Deak
(74) *Attorney, Agent, or Firm* — Fish & Richardson P.C.

(57) ABSTRACT

The present disclosure relates to a method for checking the functionality of conveying devices of a medical treatment apparatus. It further relates to a control device and/or closed-loop control device and to a medical treatment apparatus through which the method according to the present disclosure is effected, to a digital storage medium, a computer program product and to a computer program.

23 Claims, 6 Drawing Sheets

(58) Field of Classification Search
CPC ............ A61M 1/1656; A61M 2205/18; A61M 2205/3365; A61M 2205/70; A61M 1/14; F04B 51/00
See application file for complete search history.

(56) References Cited

U.S. PATENT DOCUMENTS

| | | | |
|---|---|---|---|
| 2012/0312726 | A1 | 12/2012 | Gagel |
| 2018/0308573 | A1 | 10/2018 | Hochrein et al. |
| 2019/0209766 | A1 | 7/2019 | Thiebaud et al. |
| 2022/0008634 | A1 | 1/2022 | Noack |

FOREIGN PATENT DOCUMENTS

| | | | |
|---|---|---|---|
| DE | 102019101941 | | 7/2020 |
| EP | 1319417 | A1 | 6/2003 |
| EP | 1364194 | | 7/2007 |
| JP | 2004-525375 | A | 8/2004 |
| JP | 2014-525763 | A | 10/2014 |
| JP | 2018-519888 | A | 7/2018 |
| JP | 2018-132364 | A | 8/2018 |
| WO | WO 2019/181610 | A1 | 9/2019 |

METHOD FOR CHECKING THE FUNCTIONALITY OF CONVEYING DEVICES OF A MEDICAL TREATMENT APPARATUS, AND APPARATUSES

CROSS-REFERENCE TO RELATED APPLICATIONS

The present application is the national stage entry of International Patent Application No. PCT/EP2021/070529, filed on Jul. 22, 2021, and claims priority to Application No. DE102020119654.7, filed in the Federal Republic of Germany on Jul. 24, 2020, the disclosures of which are expressly incorporated herein in their entirety by reference thereto.

TECHNICAL FIELD

The present disclosure relates to a method, a control device or closed-loop control device, and a medical treatment apparatus. Furthermore, the present disclosure relates to a digital storage medium, a computer program product, and a computer program for checking the functionality of a conveying device.

BACKGROUND

Various types of medical treatment apparatuses are known. Among the known medical treatment apparatuses are blood treatment apparatuses, in particular the apparatuses for hemodialysis, hemofiltration and hemodiafiltration. During the extracorporeal blood treatment, blood flows in an extracorporeal blood circuit through a blood treatment unit. In the apparatuses for hemodialysis, hemofiltration and hemodiafiltration, the blood treatment unit is a dialyzer or filter which, in simple terms, is separated into a blood chamber and a dialysis liquid chamber by a semipermeable membrane. During the blood treatment by hemodialysis or hemodiafiltration, the blood flows through the blood chamber, while a dialysis liquid flows through the dialysis liquid chamber.

In some blood treatment apparatuses, the dialysis liquid may be prepared by volumetric mixing. Volumetric mixing means that at least one liquid is dosed by or based on volume. For example, pure water and at least one liquid concentrate may be dosed volumetrically and mixed to fresh dialysis liquid according to a given recipe.

In volumetric dosing, the accuracy with which the conveying devices being used work, is of decisive importance. An incorrect dosage leads to an incorrect composition of the dialysis liquid. The conveyance accuracy of a conveying device may change over time. This may be caused by leaks, swelling of materials, deposits inside the conveying device and/or in the lines and wear. While leaks may be easily and reliably detected with an automatic integrity test, such as a pressure holding test, other causes, which may lead to a higher or lower flow rate, are not easily detectable automatically.

In order not to endanger patient safety, incorrect dosage must be ruled out. For this reason, the conveying devices are designed so robustly that any change in conveying capacity due to operational conditions during their service life is as small as possible. Nevertheless, the conveying capacity of a conveying device may change over time.

The conveying capacity may be checked if deviations are suspected, for example by gauging. If the conveying capacity is insufficient, the conveying device will be replaced. Such work is usually carried out by a qualified service technician.

The more often the conveying devices of the medical treatment apparatus are checked, the more reliable the treatment apparatus may function. There is a need for a regular automatic check of the conveying capacity. There is a need for automatic detection of changes in the capacity of a conveying device, for example, as part of a regular automatic function test.

SUMMARY

An object of the present disclosure is to propose a method for checking the conveying accuracy of conveying devices of a medical treatment apparatus. In addition, a control or closed-loop control device (in short: control device which can optionally also regulate) is to be proposed with which the method may be effected or initiated. In addition, further apparatuses suitable for carrying out the method, in particular a medical treatment apparatus (in short: treatment apparatus), are to be specified.

According to the present disclosure, a method for checking the functionality of a conveying device of a medical treatment apparatus for extracorporeal blood treatment is proposed.

The method preferably encompasses providing a container which is preferably completely filled with liquid. Air or another gas is preferably not provided in the container. The container is in fluid communication or conveying communication with the conveying device.

The method further encompasses setting a predetermined initial pressure in the container, preferably one which is read out of, and/or permanently stored in, a storage device. The setting may, purely exemplarily, take place using pumps and/or valves in lines which fluidically connect the container to an exterior of the container. For example, the container may initially be filled free of air using a filling pump and the ultrafiltration pump may be used to ensure a predetermined liquid pressure inside the container. The initial pressure is preferably effected by the conveying device which functionality is to be checked, preferably not by another additional conveying device which functionality is likewise to be checked. This may hereby be called defined filling, i.e. the pressure after filling is known and/or predetermined. There is preferably a difference to the atmospheric pressure.

The method encompasses controlling the conveying device to perform a predetermined or a specified number of conveying movements. Such conveying movements may be strokes, rotations, impacts, angular steps, steps, etc. of the conveying device or of its components, depending on the type of the conveying device. The controlling may be understood as a trigger of or a request for the predetermined conveying movements. These conveying movements preferably start only after the predetermined initial pressure has been set. The predetermined or fixed number of conveying movements preferably starts with the first of these conveying movements only after the initial pressure has been ensured or reached.

The method further encompasses measuring the pressure prevailing in the container by means of a pressure measuring after the predetermined number of conveying movements of the conveying device has been completed. This pressure measuring is followed by defining or designating the measured or determined pressure as the final pressure which may be assigned to the conveying device under consideration.

The method further encompasses reading-out a stored reference value from a first storage device. The reference value can be a reference pressure or a reference pressure difference. The reference value may in particular be +/−5 hpa to +/−500 hPa compared to atmospheric pressure. The first storage device may be provided as part of the medical treatment apparatus, e.g. as its internal storage, or separately therefrom.

The method further encompasses determining a pressure difference between the measured final pressure and the stored reference value. Alternatively, a pressure difference is determined between a difference between initial pressure and final pressure on the one hand and the stored reference value on the other.

The method also encompasses the step of evaluating the determined pressure difference, e.g. based on a predetermined criterion.

The result or object of the evaluation may be to determine an impermissible pressure difference between the reference value assigned to the conveying device and the measured final pressure or the determined pressure difference.

A pressure measuring at the beginning of the method may be omitted if it may be assumed with sufficient accuracy that, after the container has been filled as described above, the level of the pressure prevailing in the container after filling is already known, for example because of the filling process as such. In some embodiments, it may be provided to measure the prevailing pressure at least once, for example for control purposes, also before the conveying movements are carried out.

Optionally, the steps described supra may be performed in the order given above.

According to the present disclosure, a control device or closed-loop control device, also referred to herein in short as a control device, is proposed. It is configured in order to initiate or carry out the method according to the present disclosure in cooperation with a medical treatment apparatus.

According to the present disclosure, a medical treatment apparatus (in short: treatment apparatus) is further proposed. The treatment apparatus according to the present disclosure comprises, or is connected to, a liquid system, in particular a dialysis liquid system, with a container for liquid, a pressure measuring device (preferably an absolute pressure measuring device) for measuring a pressure prevailing in the container as well as a first storage device in which a reference value is stored. A reference value herein is in particular a reference pressure or a reference pressure difference.

The treatment apparatus according to the present disclosure further comprises a read-out device or is connected to such a device. The read-out device is configured to read out the stored reference value, which is assigned to the conveying device, from the first storage device.

Furthermore, the treatment apparatus according to the present disclosure comprises, or is connected to, a determining device. The determining device is configured to determine a pressure difference between the measured final pressure and the stored reference value, or to determine a pressure difference between a difference between the initial pressure and the final pressure on the one hand and a stored pressure difference as a stored reference value on the other.

An evaluation device, which is configured to evaluate the determined pressure difference, is also comprised by the treatment apparatus according to the present disclosure or is connected to it in signal communication. In this, the evaluation of the determined pressure difference may take place e.g. on the basis of a predetermined criterion.

The treatment apparatus comprises, or is connected to, at least one conveying device which is in fluid communication or conveying communication with the container and in particular with its contents or lumen.

A control device or closed-loop control device, in particular a control device or closed-loop control device according to the present disclosure, is also comprised by or connected to the medical treatment apparatus according to the present disclosure. The control device or closed-loop control device is configured in order to, by interacting with further devices or apparatuses of the medical treatment apparatus, induce, carry out, control and/or regulate—in particular automatically—the method according to the present disclosure, in particular as disclosed herein.

An interaction may be or may encompass an actuation, controlling or regulation. Interaction may be or may require a signal connection.

The medical treatment apparatus according to the present disclosure may, for each of the steps of the method according to the present disclosure mentioned herein, comprise, or be connected to, a correspondingly suitable and/or configured device or apparatus, such as an evaluation unit for evaluation, a pressure measuring device for pressure measuring, a filling device for filling the container (e.g. a pump, a valve or the like), etc.

A digital, in particular non-volatile, storage medium according to the present disclosure (here also denoted as carrier), in particular in the form of a floppy disk RAM, ROM, CD, hard disk, DVD, USB stick, flash card, SD card or EPROM in particular with electronically or optically readable control signals, may be configured such that to configure a control device to a control device with which the method according to the present disclosure described herein can be effected. Alternatively or in addition, the digital storage medium may be configured to configure a medical treatment apparatus into a medical treatment apparatus according to the present disclosure, with which the method according to the present disclosure described herein can be effected or carried out.

In this, all, several or some of the machine-induced steps of this method may be prompted.

A computer program product according to the present disclosure comprises a program code volatile or saved on a machine-readable carrier, by which a control device is configured such that to effect the herein described method according to the present disclosure. Alternatively or in addition, the computer program product may be used to configure a medical treatment apparatus such that the herein described method according to the present disclosure may be effected or carried out.

In this, again all, several or some of the machine-induced steps of this method may be prompted.

The term "machine-readable carrier" as used herein, refers in certain embodiments of the present disclosure to a carrier, which contains data or information interpretable by software and/or hardware. The carrier may be a data carrier, such as a diskette, a CD, DVD, a USB stick, a flashcard, an SD card, an EPROM or the like.

A computer program according to the present disclosure comprises a program code by which a control device or closed-loop control device or a medical treatment apparatus may be configured such that the herein described method according to the present disclosure may be effected or carried out.

In this, all, several or some of the machine-induced steps of this method may be prompted.

A computer program product may according to the present disclosure be understood as, for example, a computer program which is stored on a carrier, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

According to the present disclosure, a computer program may be understood as a physical, marketable software product which comprises a program.

In all of the aforementioned and following statements, the use of the expression "may be" or "may have" and so on, is to be understood synonymously with "preferably is" or "preferably has," and so on respectively, and is intended to illustrate an embodiment according to the present disclosure.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present disclosure as the interpretation that a numerical word, for example, "one" may alternatively mean "exactly one", wherever this is evidently technically possible for the person skilled in the art. Both understandings are encompassed by the present disclosure and apply to all numerical words used herein.

Whenever "programmed" or "configured" is mentioned herein, it is then disclosed that these terms are interchangeable.

Advantageous developments of the present disclosure are each also subject-matter of embodiments.

Whenever an embodiment is mentioned herein, it is then an exemplary embodiment according to the present disclosure.

When it is disclosed herein that the subject-matter according to the present disclosure comprises one or several features in a certain embodiment, it is also respectively disclosed herein that the subject-matter according to the present disclosure does, in other embodiments, likewise according to the present disclosure, explicitly not comprise this or these features, for example, in the sense of a disclaimer. Therefore, for every embodiment mentioned herein it applies that the converse embodiment, e.g. formulated as negation, is also disclosed.

Embodiments according to the present disclosure may comprise one or more of the features mentioned above and/or below in any technically possible combination.

The initial pressure is preferably that pressure with or from which the conveying device which functionality is to be checked, begins to convey.

The reference value may be stored or may have been stored e.g. by the manufacturer, for instance during production, or by the technician during commissioning and/or prior to the operation of the conveying device to be checked, in order to check the conveying device or in order to execute the method according to the present disclosure, in the first storage device which in turn may be part of the conveying device or of the medical treatment apparatus that the conveying device comprises. The invariable reference value may be read from it when the method according to the present disclosure is carried out.

The reference value is preferably not the initial pressure and/or not a pressure that was generated in order to check the functionality of another conveying device by this other conveying device.

Should the conveying device be replaced at a later time, for example for reasons of maintenance or repair, the reference value may be determined anew, just as already the case at the time of production or commissioning, and stored-preferably power-failure-proof—at a suitable location as in the first storage device, which may also be part of the method according to the present disclosure.

In order to avoid data loss (e.g. when replacing individual computer boards), copies of the stored reference value can be distributed to several computer boards.

Reference values may, for example, be stored in a Non-Volatile Random Access Memory (NOVRAM); a NOVRAM is a memory module on which may principally be written cyclically, but in which the last valid data content is still saved in the internal ROM area in the event of an external power failure. A capacitor integrated in a NOVRAM supplies the energy required to copy the content of the RAM area, which is also integrated in the NOVRAM, into the ROM area in the event of a failure of the externally applied voltage.

In several embodiments, the method according to the present disclosure further comprises the step of setting a predetermined temperature (a predetermined temperature value) inside the container in order to achieve a predetermined or fixed and, therefore, comparable state or the same general conditions for the checking, in particular the pressure measuring.

In other embodiments, the temperature prevailing in the container while the method is being carried out is measured without necessarily being set to the predetermined temperature. The measured temperature may be optionally taken into account in these embodiments, e.g. by applying correction factors to the measured pressure or by converting the measured pressure value depending on the measured temperature. The reference value may be stored and retrieved in table form, for example, depending on the temperature prevailing during the checking of the conveying device.

In some embodiments of the method, the step of evaluating encompasses or consists of determining whether the determined pressure difference or its amount is within predetermined limits, exceeds or falls below a limit value, exceeds a minimum value and/or does not exceed a maximum value. This results in an evaluation based on a criterion (limit value, range, maximum value, etc.).

In several embodiments, the method encompasses the additional step of outputting an acoustic and/or optical alarm. In particular, this alarm is output if the evaluation should lead to results that have been defined as inadmissible in advance. These results defined as inadmissible may be stored in for example a storage device. The storage device may correspond to the first storage device or be another storage device.

Alternatively or in addition, this alarm will occur in particular when predetermined limits are violated, in particular when the lower limit value is fallen below or the upper limit value is exceeded, when leaving a permissible value range or when a predetermined amount of pressure difference is exceeded.

In some embodiments, the method encompasses the additional step of storing the final pressure or the determined pressure difference in a second storage device. The second storage device may be, for example, an internal storage device of the medical treatment apparatus. It may be identical to the first storage device or different therefrom.

In several embodiments, the method encompasses the additional step of determining, a wear curve from the stored values, e.g. by calculation.

Such a curve may be evaluated, e.g. in order to be able to identify a development or a trend at an early stage on the basis of its gradient or other properties.

In some embodiments, the container comprises, or consists of, sections of the used water branch of a balancing system.

In several embodiments, the container is or comprises a section in a liquid line of a dialysis liquid system of a medical treatment apparatus.

In some embodiments, the conveying device is an ultrafiltration pump, a bicarbonate pump or a sodium pump.

In several embodiments, at least one conveying device is a displacement pump, in particular a diaphragm pump, an eccentric diaphragm pump, a tube pump, roller pump or piston pump.

In some embodiments, at least one delivery means is a flow pump. When using flow pumps, the conveyance is effected exclusively by flow-mechanical processes. Hereby, there is a permanent connection between the suction and pressure side of the pump, i.e. the medium flows freely through the machine, i.e. without flaps and valves. At standstill, the medium could flow through the pump backwards, i.e. against the pumping direction. This type includes gear pumps, impeller compressors, centrifugal pumps, etc. In these embodiments, precise volume conveyance is only possible with additional effort, for example, by a flow pump and balancing chamber. In some embodiments in which pumps of this type are used, a defined conveyance rate (for example a speed or a speed per unit of time) is preferably set, with which liquid is pressed into the system or into the container or sucked out of it, since with this type of pump no defined volume is withdrawn. The wear may be recognized on the basis of the overpressure or underpressure achieved individually by the conveying device.

In some embodiments, the medical treatment apparatus includes a heating device configured to heat the liquid present in the container to a predetermined temperature for the purpose of achieving a predetermined or specified condition or general requirements during the pressure measurement to be performed. Appropriate sensors for a feedback loop may be provided.

In several embodiments, the treatment apparatus further comprises a device which is configured to determine whether the determined pressure difference lies within predetermined limits, exceeds or falls below a limit value, exceeds a minimum value and/or does not exceed a maximum value.

In some embodiments, the treatment apparatus comprises a device for outputting an alarm. This may be configured to output an acoustic and/or optical alarm if the evaluation should yield inadmissible results. In particular when leaving predetermined limits, when falling below the lower limit value or exceeding the upper limit value, when leaving a permissible value range, when exceeding a predetermined amount, it may be provided to output such an alarm.

In several embodiments, the treatment apparatus comprises a second storage device configured to store the final pressure or the determined pressure difference in the second storage device. The second storage device may be, for example, an internal storage device of the medical treatment apparatus, it may be identical or different from the first storage device.

The second storage device may be part of the medical treatment apparatus, for example in a section that is regularly read out during maintenance activities. However, it may also be arranged remotely from the medical treatment apparatus, e.g. at a location assigned with the maintenance or monitoring of the treatment apparatus.

In some embodiments of the medical treatment apparatus, this comprises a device that is configured to determine, e.g. calculate, a wear curve from the stored values.

A medical treatment apparatus according to the present disclosure may, without being limited thereto, be suitable and/or configured for performing a blood treatment, in particular hemodialysis, hemofiltration, hemodiafiltration or separation method.

If a creeping or increasing deterioration in the conveying accuracy of a conveying device is detected over a plurality of (at least two) sequences of the method according to the present disclosure at different times, an alarm or a message may be issued in several embodiments.

For example, the medical treatment apparatus may issue a warning or an indication that maintenance, repair or replacement of the conveying device is pending due to insufficient conveying accuracy. In this way, a replacement may be made in time, i.e. before the real total failure occurs, which again may help to reduce the downtime of the treatment apparatus. A maintenance or repair of the conveying device that has been recognized as inadequate may be scheduled at an early stage and thus, unlike maintenance carried out as a reaction, not only mistimed, i.e. at a possibly inappropriate point in time.

If the method according to the present disclosure is carried out, as contemplated in some embodiments, e.g. before each treatment session in which the treatment apparatus is used or at any short intervals, the point in time at which maintenance or repair of the inadequate conveying device is best tackled may be identified comparatively early. The point in time at which disturbance of the operation of the treatment apparatus due to the inadequate conveying device will occur, may advantageously be largely predictable by the method according to the present disclosure using appropriate evaluation of the measured values or results obtained.

In several embodiments, the results of the method according to the present disclosure (as evaluation results, the deviation from an actual conveying activity, etc.) are shown, e.g. on the treatment apparatus (display) or on an external monitor, display or the like, or printed out.

In several embodiments, the results or at least the results of the method according to the disclosure recognized as relevant are stored and/or further processed in a data storage in a retrievable manner after execution of said method on the treatment apparatus. This data memory may be part of the medical treatment apparatus or be provided separately from it. The results can be processed further in order to create a wear curve over time in relation to the conveying device. This curve may be read out for example by a service technician, if necessary. Alternatively, the data memory may be available on an external device. Thus, results may be fed into a network and stored there. If necessary, the results may then be retrieved from several devices.

In some embodiments, a probability of the occurrence of a disturbance or failure due to a malfunction of one or of each conveying device is determined according to known methods and communicated, e.g. by storing in the readable data memory, by display, alarm, etc. In addition or alternatively, the time point or time period at which such a disturbance is likely to occur can be determined and communicated.

In several embodiments, known methods of trend analysis are used to determine, among other things, the probability of the occurrence of a disturbance, or point of time or duration thereof, due to a malfunction of a conveying device.

The hardware or software required to carry out the above-mentioned determination of the probability, point in time/duration and/or the display and/or transmission of the results based thereupon is optionally provided and set up, configured and/or programmed accordingly.

By using trend analysis, trends—i.e. medium- or long-term developments—may be determined and optionally quantified.

Well-known methods of trend analysis encompass simple averaging, the determination of moving averages, the determination of the smallest square deviation, first-order exponential smoothing, etc.

In some embodiments, the container comprises at least one line section. Alternatively, it comprises a plurality of line sections which are in fluid communication with each other and which are preferably part of the treatment apparatus, in particular its dialysis liquid system. Such line sections may be in fluid communication with one another in such a way that a fluid pressure prevailing in them may be set or adjusted unhindered within the combination of lines.

In several embodiments, the container is a vessel. What is stated herein about the container also applies in these embodiments undiminished to its design as a vessel.

In several embodiments the liquid is dialysis liquid. In some preferred embodiments, the liquid is pure, degassed water without additives (RO water, reverse osmosis water).

Based solely on the evaluation of the measured values of the pressure measuring, it can be determined in some embodiments whether the conveying device conveys inaccurately and what amounts the deviations have. Furthermore, in other embodiments it may be determined whether the conveying device will deliver imprecisely (or, in the worst case, not at all) in the foreseeable future. A timely exchange of the conveying device may then advantageously be initiated.

Since the method according to the present disclosure described herein can be carried out with the medical treatment apparatus according to the present disclosure and the treatment device is configured to carry it out using its control device, reference is made to the above-described statements regarding the method and its execution in order to avoid repetitions.

In some embodiments, none of the three conveying devices conveys into the container while the method according to the present disclosure is running, or as a step of the method.

In several embodiments, none of the three conveying devices convey into the container unless this serves to completely fill the container with liquid.

In some embodiments, none of the three conveying devices convey into the container, unless this serves to set the predetermined initial pressure before the conveying device in question is activated in order to perform the desired conveying activity required to convey the predetermined volume of liquid.

In several embodiments, the conveying device conveys within the scope of the method according to the present disclosure, starting always from the same initial pressure. An increase in the pressure in the container by the conveying device is not provided in these embodiments.

In some embodiments, the container is always the same when the conveying device is checked. The initial pressure prevailing in it may always be the same, but this is not necessarily the case.

In several embodiments, absolute values of a single pressure or differences between pressures are considered.

When a measuring of a pressure is mentioned here, this term may in several embodiments also include the determination of the pressure sought, for example by calculating the pressure from available values.

In some embodiments, no volume is measured, compared and/or evaluated.

In several embodiments, only the function of exactly one conveying device is tested up to and including the step of evaluating the determined pressure difference.

In some embodiments, up to and including the step of evaluating the determined pressure difference, only exactly one conveying device is used or only exactly one conveying device is conveying, in particular only one conveying device which is to be checked.

When a signal communication or communication connection between two components is mentioned here, this may be understood to mean a connection that exits during use. It may also be understood that a preparation for such a (wired, wireless or otherwise implemented) signal communication exists, for example by coupling both components, for example by pairing, etc.

Pairing is a process that takes place in connection with computer networks in order to establish an initial link between computer units for the purpose of communication. The best-known example of this is the establishing of a Bluetooth connection, by which various devices (e.g. smartphone, headphones) are connected to each other. Pairing is sometimes also referred to as bonding.

In some embodiments, the method according to the present disclosure does not encompass calculating the initial liquid volume and/or the initial volume of air present in the container.

In several embodiments, the container is not or does not comprise a mixing chamber.

In some embodiments, the treatment apparatus comprises rollers for its movement. In several embodiments, the treatment apparatus comprises a touch screen for use by the medical staff.

By some embodiments according to the present disclosure, one or more of the advantages mentioned herein may be achieved, including the following:

By using the method according to the present disclosure, a reliable statement can be made about the functional efficiency and in particular the conveying accuracy of the conveying device in question, preferably by comparing measured pressure values or differences with stored reference values.

A further advantage of the present disclosure is that a medical treatment apparatus is enabled to automatically carry out the check for sufficient accuracy of the conveying activity of its conveying devices. Assigning a qualified service technician or a user is not necessary for this purpose or may be limited to occasional checks, which may also contribute to cost savings.

In addition, deviations in the conveying activity of a conveying device that occur for the first time between visits by the qualified service technician or checks by the user can be detected at an early stage, for example as part of a daily routine check.

Another advantage is the improvement in the user-friendliness of a generic blood treatment apparatus. According to the present disclosure, the user is not burdened with checking and correcting the conveying capacity of conveying devices. Downtimes of the blood treatment apparatus while a qualified service technician is on duty for checking purposes, for example by weighing or using measuring cylinders, are not necessary or are less necessary.

Since the procedure according to the present disclosure is based on a defined filling (pressure, possibly also temperature) of a container, which in practice will have to be filled anyway for reasons other than the inspection of the conveying device, a part of the work necessary for the implementation of the present method may be advantageously omitted: at least the first filling should already have taken place anyway in many practical applications.

The method according to the present disclosure may enable to check the conveying volumes of the pumps without great additional effort. By storing the determined pressure values and pressure differences and creating a wear curve, predictions can be made about a possible failure in the near future. In this way, a service technician could query the expected remaining service life of the pump during the next safety inspection and, if necessary, replace the pump prematurely. This advantageously contributes to reducing service calls and thus saving costs.

With the present disclosure, any damage that may have occurred which can affect the pumping operation, e.g. detached, torn or damaged membranes, for example due to wear, may also be determined, which is particularly relevant in using eccentric membrane pumps. The number of elaborate/complex consuming tests of the pumps by a service technician can thus be advantageously reduced or eliminated entirely.

The early recognition of the need to replace the conveying device may thus increase the reliability of the medical treatment apparatus, because the more precisely the conveying device of the treatment apparatus conveys, the safer this can work for the patient.

Furthermore, it may be advantageous that the statistical evaluation of failure figures relating to the conveying device in question can be improved by the method according to the present disclosure. This helps advantageously to determine real errors and to reduce or completely eliminate the number of undetected nonfunctional conveying devices.

Finally, it may be an advantage that by the present disclosure conveying devices can be checked, even if the medical treatment apparatus is not provided with a mixing chamber, in particular a mixing chamber with its own monitoring sensor technology, which could be used for checking conveying devices, as may be the case in several embodiments.

BRIEF DESCRIPTION OF THE DRAWINGS

The present disclosure is described below on the basis of preferred embodiments thereof with reference to the attached drawing. The method according to the present disclosure and the blood treatment apparatus according to the present disclosure are described using the example of a hemodialysis apparatus. The method according to the present disclosure may however also be used in the same way in other blood treatment apparatuses, for example a hemodiafiltration apparatus. In the figures, the following applies.

DETAILED DESCRIPTION

Figure 1:
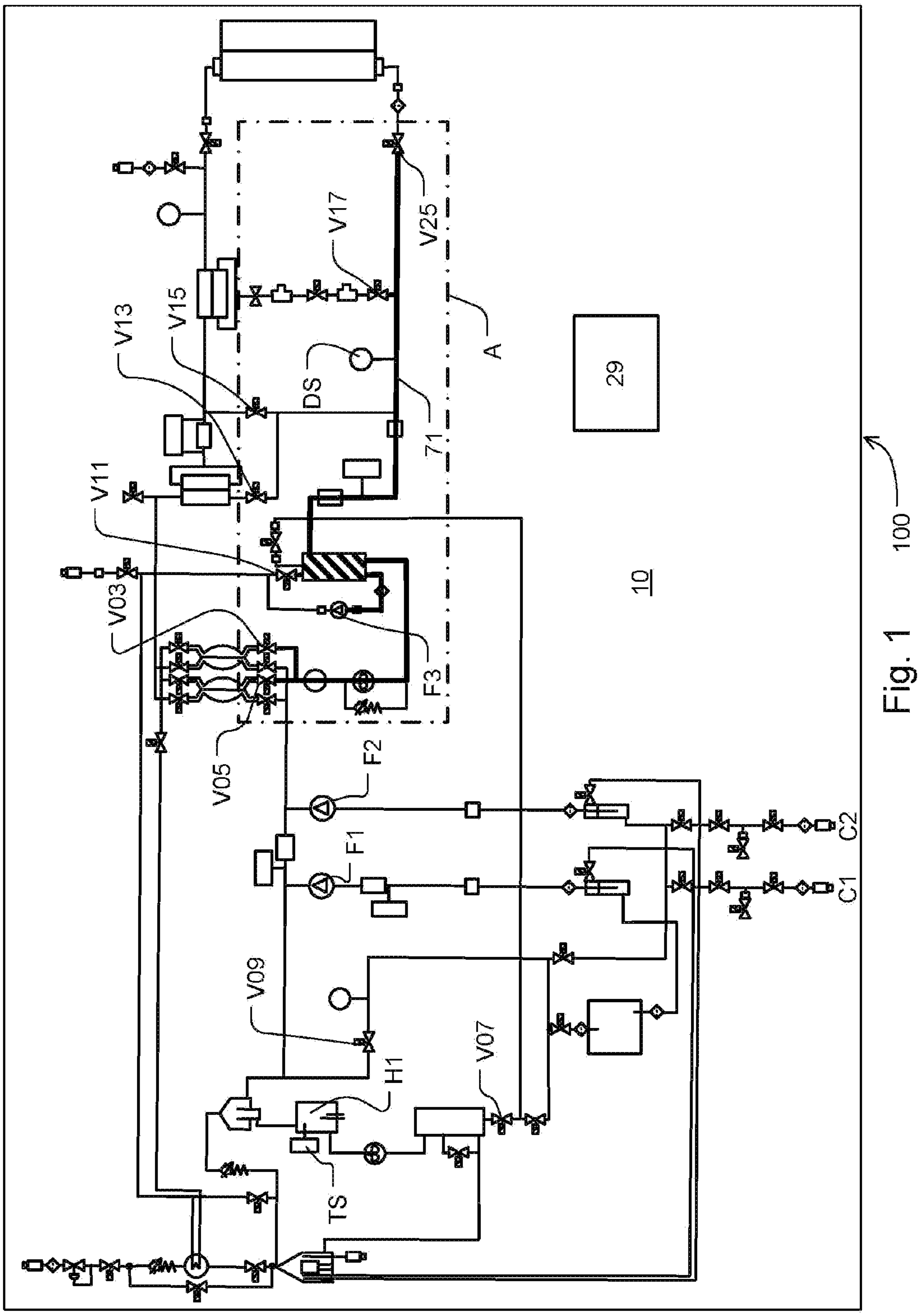
FIG. 1 shows parts of a line diagram of a liquid system of a medical treatment apparatus according to the present disclosure in a first embodiment.

FIG. 1 shows parts of a line diagram of a dialysis liquid system 10 (also referred to as hydraulics)—as an example of a liquid system—of a medical treatment apparatus 100 according to the present disclosure in a first embodiment, here purely optionally of a blood treatment apparatus.

The dialysis liquid system 10 comprises a plurality of pumps, valves, actuators, sensors and other components. All of them may be independently connected in signal communication to a control device or closed-loop control device 29 of the medical treatment apparatus 100 and may optionally be controlled and/or read-out by it.

The pumps mentioned above include amongst others a first conveying device F1, here a bicarbonate pump, a second conveying device F2, here a sodium pump, as well as the ultrafiltration pump designated here as conveying device F3.

The pumps are integrated in fluid communication with each other in the dialysis liquid system 10. The conveying device F3 is fluidically connected to a ventilation device and to a temperature sensor TS as well as to a pressure sensor DS via the lines which are extracted in FIG. 1*a* and shown here and in FIG. 1*a* in bold. The lines connecting them are fluidically separated from an outside by the (halted) conveying device F3 on the one hand and by the (closed) valves V03, V05, V11, V13, V15, V17 and V25 on the other hand. The volume limited by the above-mentioned conveying device F3 and the valves V11, V13, V15, V17 and V25 thus results in a closed vessel or a compound of closed but communicating lines, in particular line sections, or vessels, and is referred to herein as a container. Other designations, such as volume, receiving section for liquid, etc., would also be conceivable in the context of the present disclosure instead of "container".

Figure 1A:
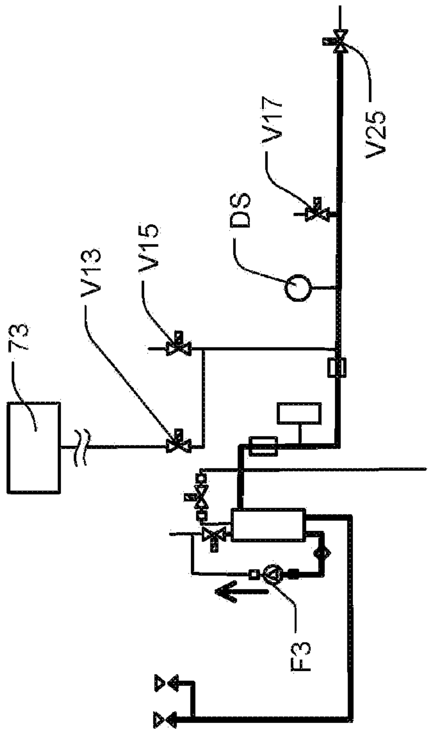
FIG. 1*a* shows section A of the liquid system of the medical treatment apparatus of FIG. 1, including the container shown in FIG. 1.

The container shown in FIG. 1*a* while omitting those elements from FIG. 1 that are not involved in creating its closed volume, is referred to herein as container 71, see FIG. 1*a*.

The conveying device F3 is arranged with respect to the container 71 such that it may convey the liquid that is present in the container 71 out of the latter, which it also does in the course of the method according to the disclosure in an exemplary embodiment described below.

The pressure gauge DS arranged in the container by which e.g. the pressure measuring may be carried out, may optionally have the highest measuring accuracy of all pressure gauges measuring in the container, like any other pressure sensor used. The utilized pressure gauge may be an analog-digital converter (ADC).

The control device or closed-loop control device 29 may, in cooperation with the temperature sensor TS and a heating device H1, regulate the internal temperature of the container 71 to a predetermined temperature. The predetermined temperature may correspond to a temperature at which a reference value P_R (see FIG. 4) was determined during production of the conveying device and may have a value in degrees Celsius (C.°).

The medical treatment apparatus may encompass other valves, for example the V03, V05, V07 or V9. The container 71 may if necessary be expanded and/or relocated by these valves, for example to check a different conveying device F1, F2 than the conveying device F3 of the example described above. An expanding is to be understood such that the container 71 encompasses more line sections of the treatment system 100 than in the example described above. Relocating is to be understood such that the container 71 encompasses other line sections of the treatment system 100 than in the example described above, as shown in FIG. 1*b*.

FIG. 1*a* shows the container from FIG. 1. Components of FIG. 1 that are not involved in the creation of the closed container 71 are not shown again in FIG. 1*a* for a better overview.

For filling it, the container 71 is filled in some embodiments using a liquid source 73 (see FIG. 1*a*) via hydraulic lines. The liquid source 73 may be or may comprise a source for water, in particular a water tap or a water line, optionally with subsequent devices for cleaning or degassing. In other embodiments, the refilling may optionally be done from an external sealed or closed source, for example a liquid bag. The method according to the present disclosure may encompass filling or may only begin when a filled container 71 is present.

The filling defines an initial pressure P_0 within the container 71, which may be controlled or set by using the liquid source 73, alternatively or additionally, for example, via valve V13, especially if the filling has been carried out by a pump in an undefined way. The other valves, which delimit the container 71, are hereby optionally closed.

Optionally, each valve connected to the container 71 may, for this purpose, be opened and closed again for filling; the other valves of the container 71 are preferably closed.

FIG. 1 and FIG. 1*a* are mainly dedicated to the conveying device F3. This is purely exemplary. What is stated here for F3 can also apply analogously to F1 and/or F2 (see FIG. 1*b*).

Figure 1B:
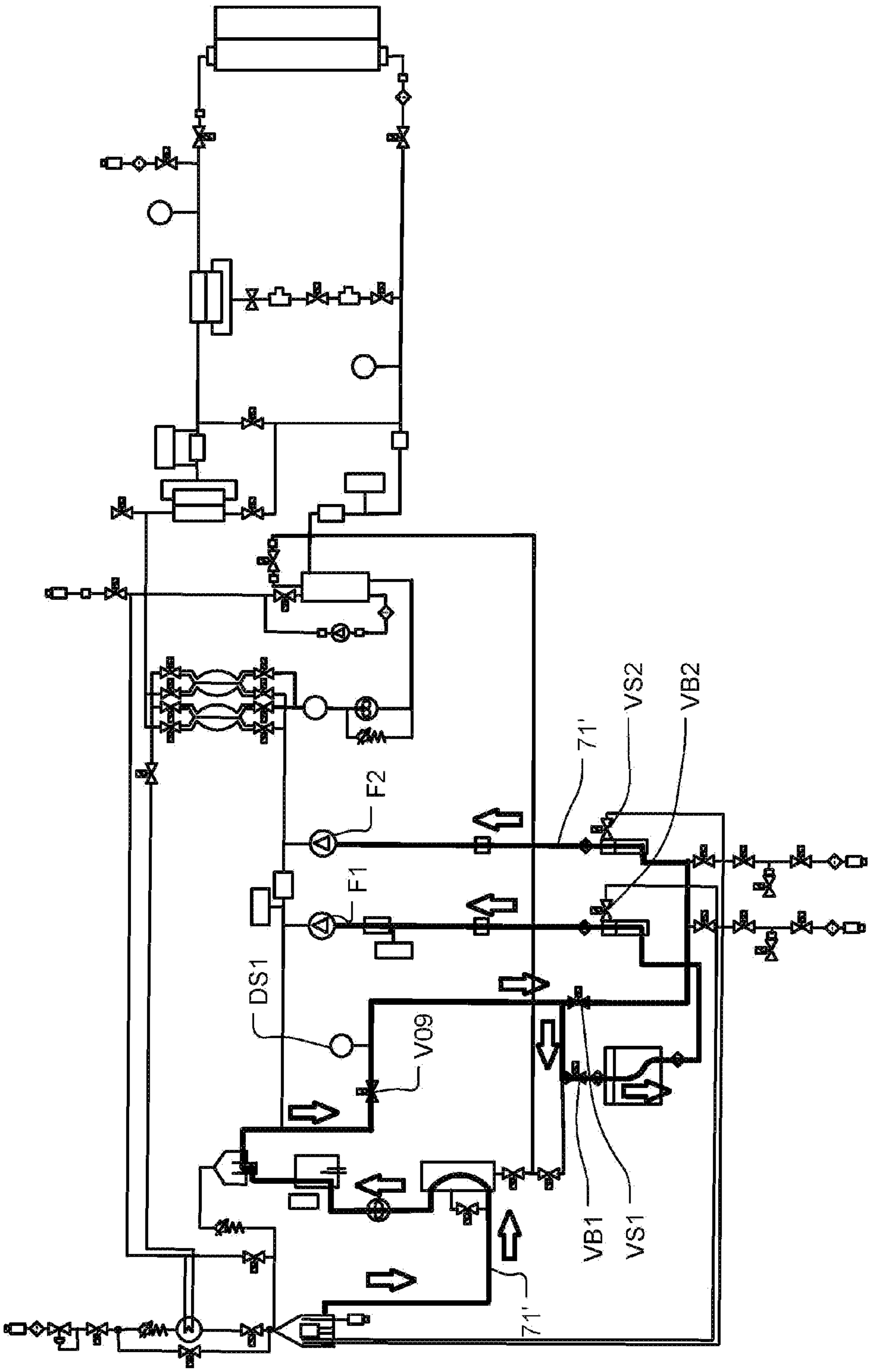
FIG. 1*b* shows an alternative container, which is suitable for checking alternative conveying device with respect to FIG. 1.

FIG. 1*b* shows in the line diagram of the dialysis liquid system 10 from FIG. 1 an alternative container 71', which is suitable for checking the conveying devices F1, F2.

For this purpose, the valves VB2, VS2 and V09 are closed. If necessary, valves VB1 and VS1 will allow or enable access to the pressure sensor DS1.

The statements made above about the container 71 also apply analogously undiminished to the container 71'.

The liquid for filling the container 71' may originate from the liquid source 73 shown at the top left.

Figure 2:
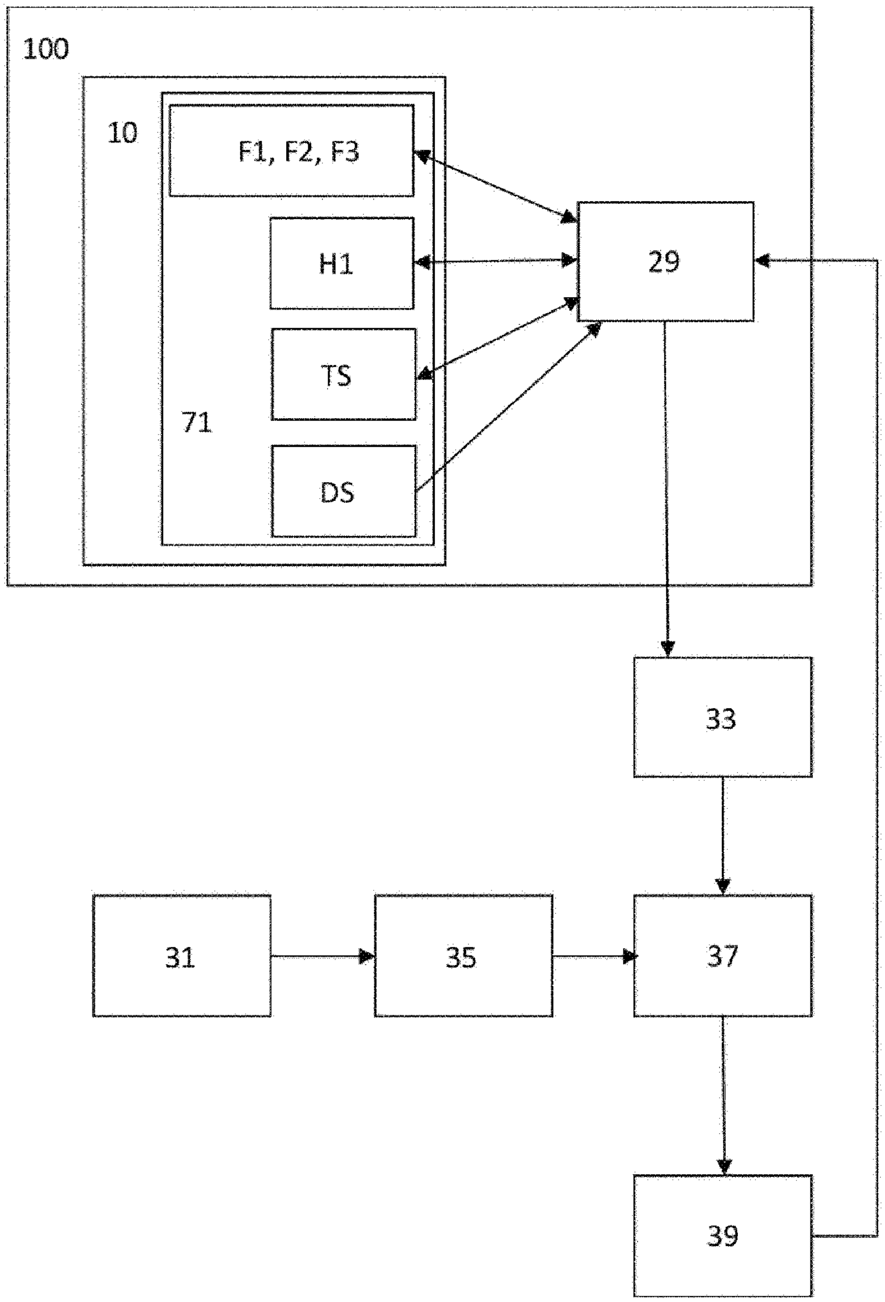
FIG. 2 shows, schematically simplified, the course of the method according to the present disclosure on the basis of the devices used for this purpose.

FIG. 2 shows, in a schematically simplified manner, the course of the method according to the present disclosure on the basis of the devices used for this purpose.

At the top left in FIG. 2, an exemplary medical treatment apparatus 100 with a dialysis liquid system 10 is shown in a highly simplified schematic manner. The control device or closed-loop control device 29 may be configured to effect in cooperation with the temperature sensor TS and the heating device H1 a predetermined internal temperature of the container 71, 71'. By activating the valves (not shown in FIG. 2) or the conveying devices F1, F2, F3 by the control device or closed-loop control device 29, a predetermined initial pressure P_0 may be set in the interior of the container 71, 71'; this may possibly be controlled by the pressure sensor DS.

Figure 4:
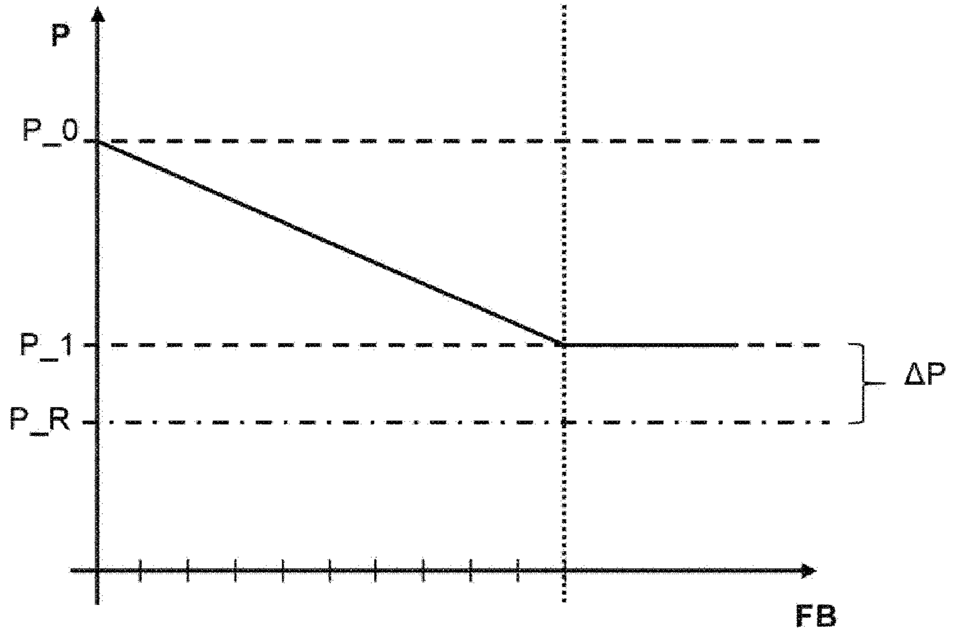
FIG. 4 shows an exemplary course of the method according to the present disclosure in a pressure/conveying movement diagram.

In order to check it, the conveying device F3, here the ultrafiltration pump, is induced by the control device or closed-loop control device 29 to execute a predetermined number of conveying movements FB (see FIG. 4). Depending on the embodiment of the conveying device, these may be strokes, rotations or impacts or beats, for example five strokes.

After completion of the predetermined number of conveying movements FB, the pressure inside the container 71, 71' is measured by the pressure gauge DS. It may be transmitted, in particular by the control device or closed loop control device 29, to the optionally available second storage device 33 to be stored therein.

The reference value P_R, which corresponds to the conveying device F3 and is stored in the first storage device 31, and which may be a reference pressure or a reference pressure difference, is read out by the read-out device 35.

The determining device 37 may be configured to determine a pressure difference ΔP between the measured final pressure P_1 and the stored reference pressure P_R. Alternatively, it may be provided that a pressure difference ΔP is determined between a difference between initial pressure P_0 and final pressure P_1 on the one hand and the stored reference value P_R, which in this case is a reference pressure difference, on the other hand.

An evaluating device 39 may be configured to evaluate the determined pressure difference ΔP. It may be provided to transmit the result of the evaluation to the medical treatment apparatus 100, in particular to its control device or closed-loop control device 29.

The medical treatment apparatus 100 or the control device or closed-loop control device 29 may in particular be provided to activate an optional alarm device (not shown in FIG. 2) if the amount of the determined pressure difference ΔP is e.g. outside predetermined limits or otherwise does not meet a predetermined criterion.

Figure 3:
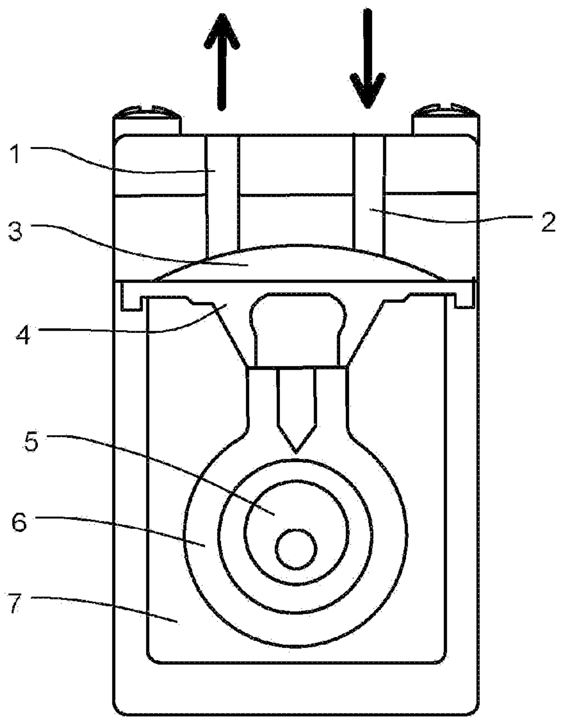
FIG. 3 shows, schematically simplified, an eccentric membrane pump as an exemplary embodiment of a conveying device.

FIG. 3 shows, in a schematically simplified manner, an eccentric diaphragm pump as an exemplary embodiment of the conveying device F1, F2 or F3 in a schematic representation.

An elastic membrane 4 is moved up and down by an eccentric 5 and a connecting rod 6.

In the downward stroke it sucks in the fluid to be conveyed via an inlet valve 2. In the upward stroke, the membrane 4 pushes the fluid out of the pump head via an outlet valve 1. A downward stroke, an upward stroke, or a combination of exactly one downward stroke with exactly one subsequent upward stroke may each correspond to a conveying movement FB.

A conveying room 3 is hermetically separated from a pump drive 7 by the membrane 4.

According to the present disclosure, the pressure generated in the conveying room 3 is a negative pressure (underpressure), by which a tearing of the membrane 4 of the conveying device may advantageously be recognized, since in the case of underpressure, the membrane 4 is prevented from resting on the plunger. If an overpressure were to prevail in conveying room 3, it would always force the membrane 4 against the plunger and a tearing could remain undetected in such a case.

FIG. 4 shows an exemplary course of the method according to the present disclosure in a pressure [P] over a number of conveying movements [FB] diagram, wherein reference is made to the arrangement of FIG. 1 and FIG. 1*a*.

In FIG. 4, the following applies:

P_0 is the predetermined initial pressure, an absolute pressure; P_0 may be measured by a pressure measuring using an absolute pressure gauge, it may be calculated or known from or based on other circumstances.

P_1 is the pressure prevailing in container 71 after the completion of the conveying movement of the conveying device in question and is referred to herein as final pressure.

P_R is a negative reference value for the pressure (underpressure) in the container 71, i.e. a negative pressure value at which the final pressure is measured, after a predetermined number of conveying movements FB of the conveying device, or the pressure difference between the pressure before the conveying movement on the one hand and the pressure after the conveying movement on the other hand. The reference value is advantageously determined at the factory under at least one defined state of the container or at least one defined general condition. A general condition may be for example an internal temperature of the container 71, wherein it may also be provided here to define a narrow temperature range as permissible.

The method begins after the initial pressure P_0 in the container 71 is set to the initial pressure P_0 at optionally a defined or predetermined internal temperature or within a predetermined, narrow temperature range (see FIG. 1), which may be done by the liquid source 73 and at least one conveying device of the medical treatment apparatus 100 and may be checked if necessary by the pressure gauge DS or the temperature gauge TS, respectively.

The conveying device F3 conveys liquid out of the container 71, here exemplarily in ten strokes, which is why the pressure gauge DS or another pressure sensor detects a drop in the pressure prevailing in the container 71 down to P_1, the final pressure, after completion of conveyance by the conveying device F3, i.e. after ten strokes.

In the example shown, there is a pressure difference ΔP between the final pressure P_1 and an already stored reference value P_R. In this example, the reference value P_R stands for a pressure that was (pre) determined (by the factory) after 10 strokes by way of example.

The determined final pressure P_1 lies above the clearly more negative reference value P_R, here exemplarily an underpressure, in other embodiments it could also be an overpressure. An alarm may be provided for the case that the amount of the pressure difference ΔP exceeds a certain value, leaves a permissible value range, or violates another criterion. Such an alarm may occur acoustically or optically or, in some embodiments, could already include the indication that the conveying device F3 is at least limited in terms of its functionality.

If no alarm is issued, the achieved final pressure P_1 or the determined pressure difference ΔP is stored in the second storage device 33 (see FIG. 2).

It may be provided to calculate a wear curve from several final pressures P_1 or pressure differences ΔP over time and to store it if necessary. The wear curve may be stored such that it may be read out or displayed by a service technician at any time.

LIST OF REFERENCE NUMERALS

100 medical treatment apparatus
1 outlet valve
2 inlet valve
3 conveying room
4 membrane
5 eccentric
6 connecting rod
7 pump drive
10 dialysis liquid system
29 control device or closed-loop control device
31 first storage device
33 second storage device
35 read-out device
37 determining device
39 evaluation device
71 container
71' container
73 liquid source
F1 first conveying device, here exemplarily: bicarbonate pump
F2 second conveying device, here exemplarily: sodium pump
F3 third conveying device, here exemplarily: ultrafiltration pump
FB conveying movements
DS pressure gauge, pressure measuring device
DS1 pressure gauge
TS temperature gauge, temperature sensor
C1 first concentrate container
C2 second concentrate container
H1 heating device
P_0 initial pressure
P_1 final pressure
P_R reference value
ΔP (pressure)difference
t time
V03 valve
V05 valve
V07 valve
V09 valve
V11 valve
V13 valve
V15 valve
V17 valve
V25 valve
VB1, VB2 valves
VS1, VS2 valves

The invention claimed is:

1. A method for checking a functionality of a conveying device of a medical treatment apparatus for an extracorporeal blood treatment, the method comprising:

providing a container filled with liquid, wherein the container is in fluid communication or conveying communication with the conveying device;

setting a predetermined initial pressure (P_0) inside the container;

controlling the conveying device to perform a predetermined number of conveying movements;

after completion of the predetermined number of conveying movements of the conveying device, measuring a pressure prevailing in the container using a pressure measuring device and defining the measured pressure as a final pressure (P_1), wherein the initial pressure (P_0) is set and the final pressure (P_1) is measured when an internal temperature of the container is set to a predetermined temperature value at which a reference value (P_R) has been measured;

receiving, from a first storage device, the stored reference value (P_R) comprising a reference pressure or a reference pressure difference;

determining a pressure difference (ΔP), wherein the pressure difference (ΔP) equals either:

a difference between the final pressure (P_1) and the stored reference value (P_R), or a difference between: (i) a difference between the initial pressure (P_0) and the final pressure (P_1) and (ii) a difference between the initial pressure (P_0) and the stored reference value (P_R); and evaluating the determined pressure difference (ΔP).

2. The method of claim 1, further comprising:

setting the internal temperature of the container to reach the predetermined temperature value while setting the initial pressure (P_0) and measuring the final pressure (P_1).

3. The method of claim 1, wherein evaluating the determined pressure difference (ΔP) comprises:

determining whether the determined pressure difference (ΔP) lies within predetermined limits, exceeds or falls below a limit value, exceeds a minimum value, or does not exceed a maximum value.

4. The method of claim 1, further comprising:

outputting an acoustic alarm or an optical alarm in response to determining at least one of (i) results of evaluating the determined pressure difference (ΔP) correspond to results defined as inadmissible in advance, (ii) predetermined limits are violated by the determined pressure difference (ΔP), (iii) the pressure difference (ΔP) falls below a lower limit value or exceeds an upper limit value, (iv) an admissible value range is exceeded by the determined pressure difference (ΔP), or (v) a predetermined amount is exceeded by the determined pressure difference (ΔP).

5. The method of claim 1, further comprising:

storing the final pressure (P_1) or the determined pressure difference (ΔP) in a second storage device.

6. The method of claim 5, further comprising:

determining a wear curve from values stored on the second storage device.

7. The method of claim 1, wherein the container comprises sections of a used water branch of a balancing system.

8. The method of claim 1, wherein the container comprises a section in a liquid line of a dialysis liquid system.

9. The method of claim 1, wherein the conveying device is an ultrafiltration pump, a bicarbonate pump, or a sodium pump.

10. The method of claim 1, wherein the conveying device is a displacement pump, a membrane pump, an eccentric membrane pump, a tube pump, a roller pump, or a piston pump.

11. A control device or a closed-loop control device configured to initiate or carry out, in interaction with a medical treatment apparatus, a method comprising:

setting a predetermined initial pressure (P_0) inside a container filled with liquid, wherein the container is in fluid communication or conveying communication with a conveying device;

controlling the conveying device to perform a predetermined number of conveying movements;

after completion of the predetermined number of conveying movements of the conveying device, measuring a pressure prevailing in the container using a pressure measuring device and defining the measured pressure as a final pressure (P_1), wherein the initial pressure (P_0) is set and the final pressure (P_1) is measured when an internal temperature of the container is set to a predetermined temperature value at which a reference value (P_R) has been measured;

receiving, from a first storage device, the stored reference value (P_R) comprising a reference pressure or a reference pressure difference;

determining a pressure difference (ΔP), wherein the pressure difference (ΔP) equals either:

a difference between the final pressure (P_1) and the stored reference value (P_R), or a difference between: (i) a difference between the initial pressure (P_0) and the final pressure (P_1) and (ii) a difference between the initial pressure (P_0) and the stored reference value (P_R); and evaluating the determined pressure difference (ΔP).

12. A medical treatment apparatus comprising or connected to:

a liquid system comprises a container for liquid;

a pressure measuring device for measuring a pressure prevailing in the container, the measured pressure being defined as a final pressure (P_1);

a first storage device storing a reference value (P_R), wherein the reference value (P_R) comprises a reference pressure or a reference pressure difference;

a read-out device configured to read out the reference value (P_R) stored on the first storage device;

an evaluation device configured to evaluate a determined pressure difference (ΔP);

at least one conveying device in fluid communication or conveying communication with the container); and a control device or closed-loop control device configured to initiate execution of a method comprising:

setting a predetermined initial pressure (P_0) inside the container;

controlling the at least one conveying device to perform a predetermined number of conveying movements;

after completion of the predetermined number of conveying movements of the conveying device, measuring a pressure prevailing in the container using the pressure measuring device and defining the measured pressure as a final pressure (P_1), wherein the initial pressure (P_0) is set and the final pressure (P_1) is measured when an internal temperature of the container is set to a predetermined temperature value at which the reference value (P_R) has been measured;

receiving, from the first storage device, the stored reference value (P_R);

determining the pressure difference (ΔP), wherein the pressure difference (ΔP) equals either:

a difference between the final pressure (P_1) and the reference value (P_R), or a difference between: (i) a difference between the initial pressure (P_0) and the final pressure (P_1) and (ii) a difference between the initial pressure (P_0) and the reference value (P_R); and evaluating the determined pressure difference (ΔP).

13. The medical treatment apparatus of claim 12, comprising a heating device configured to heat a liquid with which the container is being filled or will be filled to the predetermined temperature while setting the initial pressure (P_0) and measuring the final pressure (P_1).

14. The medical treatment apparatus of claim 12, wherein evaluating the determined pressure difference (ΔP) comprises determining whether the determined pressure difference (ΔP) lies within predetermined limits, exceeds or falls below a limit value, exceeds a minimum value, or does not exceed a maximum value.

15. The medical treatment apparatus of claim 12, further comprising a device for outputting an alarm, the device being configured to output an acoustic alarm or an optical alarm or another alarm in response to determining at least one of (i) results of evaluation of the determined pressure difference (ΔP) correspond to inadmissible results, (ii) predetermined limits are violated by the determined pressure difference (ΔP), (iii) the determined pressure difference (ΔP) falls below a lower limit value or exceeds an upper limit value, (iv) an admissible value range is not met by the determined pressure difference (ΔP), or (v) a predetermined value is exceeded by the determined pressure difference (ΔP).

16. The medical treatment apparatus of claim 12, further comprising a second storage device configured to store the final pressure (P_1) or the determined pressure difference (ΔP) in the second storage device.

17. The medical treatment apparatus of claim 16, further comprising a device configured to determine a wear curve from the values stored on the second storage device.

18. The medical treatment apparatus of claim 12, wherein the container comprises sections of a used water branch of a balancing system.

19. The medical treatment apparatus of claim 12, wherein the container comprises a section in a liquid line of the liquid system.

20. The medical treatment apparatus of claim 12, wherein the conveying device is an ultrafiltration pump, a bicarbonate pump or a sodium pump.

21. The medical treatment apparatus claim 12, wherein the conveying device is a displacement pump, a membrane pump, an eccentric membrane pump, a tube pump, a roller pump, or a piston pump.

22. The medical treatment apparatus of claim 12, wherein the medical treatment apparatus comprises a hemodialysis apparatus, a hemofiltration apparatus, a hemodiafiltration apparatus, or an apparatus for carrying out a separation method.

23. A computer-readable storage medium comprising instructions for execution of a method according to claim 1.

* * * * *